United States Patent
Raines et al.

(10) Patent No.: US 7,122,521 B2
(45) Date of Patent: Oct. 17, 2006

(54) COLLAGEN MIMICS

(75) Inventors: Ronald T. Raines, Madison, WI (US); Jonathan A. Hodges, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 286 days.

(21) Appl. No.: 10/874,725

(22) Filed: Jun. 23, 2004

(65) Prior Publication Data

US 2005/0004032 A1 Jan. 6, 2005

Related U.S. Application Data

(60) Provisional application No. 60/480,678, filed on Jun. 23, 2003.

(51) Int. Cl.
*A61K 38/00* (2006.01)
*A61K 38/06* (2006.01)
*C07K 5/00* (2006.01)

(52) U.S. Cl. .............. 514/12; 514/2; 530/331; 530/329; 530/345; 530/356

(58) Field of Classification Search .............. None
See application file for complete search history.

(56) References Cited

U.S. PATENT DOCUMENTS 5,973,112 A * 10/1999 Raines

OTHER PUBLICATIONS

Bella, J. et al., "Crystal and Molecular Structure of a Collagen-Like Peptide at 1.9 A Resolution," Science (1994) 266:75-81.
Bretscher, L.E. et al., "Conformational Stability of Collagen Relies on a Stereoelectronic Effect," J. Am. Chem. Soc. (2001) 123:777-778.
Eberhardt, E.S. et al., "Inductive Effects on the Energetics of Prolyl Peptide Bond Isomerization: Implications for Collagen Foling and Stability," Journal of the American Chemical Society, (1996) 118:12261-12266.
Gottieb, A.A., et al., "Incorporation of cis- and trans-4-Fluoro-L-prolines into Proteins and Hydroxylation of the trans Isomer During Collagen Biosynthesis," Biochemistry (1965) 4:2507-2513.
Hodges, J.A. et al., "The Effect of Fluoroproline in the X-Position of the Stability of the Collagen Triple Helix," Abstract, Americal Peptide Symposium Jul. 23, 2003.
Holmgren, S.K. et al., "Code for collagen's stability deciphered," Nature (1998) 392:666-667.
Panasik, N., Jr. et al., "Inductive effects on the structure of proline residues," Int. J. Peptide Protein Res. (1994) 44:262-269.
Sakakibara, S., et al., "Synthesis of (Pro-Hyp-Gly)n of defined molecular weights Evidence for the stabilization of collagen triple helix by hydroxypyroline," (1973) 303:198-202, Biochimica ef Biophysica Acta (1973) vol. 303 pp. 198-202.

* cited by examiner

*Primary Examiner*—B. Dell Chism
(74) *Attorney, Agent, or Firm*—Quarles & Brady LLP

(57) ABSTRACT

A novel collagen mimic comprising a tripeptide unit having the formula $(flpYaaGly)_n$, where flp is 4(S)-fluoro-L-proline, is disclosed. The collagen mimic has increased stability relative to the collagen-related triple helices $(ProYaaGly)_n$, $(hypYaaGly)_n$, and $(HypYaaGly)_n$.

10 Claims, 4 Drawing Sheets

COLLAGEN MIMICS

CROSS-REFERENCE TO RELATED APPLICATIONS

This application claims priority from U.S. provisional patent application No. 60/480,678 filed Jun. 23, 2003.

STATEMENT REGARDING FEDERALLY SPONSORED RESEARCH OR DEVELOPMENT

This invention was made with government support under grant AR 44276, awarded by the National Institutes of Health, and by a National Institutes of Health postdoctoral fellowship AR48057. The United States Government has certain rights in this invention.

BACKGROUND

Collagen is the most abundant protein in vertebrates, occurring in virtually every tissue, including skin, tendon, bone, blood vessel, cartilage, ligament, and teeth. Collagen serves as the fundamental structural protein for vertebrate tissues. Collagen abnormalities are associated with a wide variety of human diseases, including arthritis, rheumatism, brittle bones, atherosclerosis, cirrhosis, and eye cataracts. Collagen is also critically important in wound healing. Increased understanding of the structure of collagen, and of how its structure affects its stability, facilitates the development of new treatments for collagen-related diseases and improved wound healing treatments.

Collagen is a fibrous protein consisting of three polypeptide chains that fold into a triple helix, Jenkins, C. L., Raines, R. T. *Nat. Prod. Rep.* 19: 49–59 (2002). Mammals produce at least 17 distinct polypeptide chains that combine to form at least 10 variants of collagen. In each of these variants, the polypeptide chains of collagen are composed of approximately 300 repeats of the tripeptide sequence X-Y-Gly, where X is often a proline (Pro) residue and Y is often a 4(R)-hydroxyproline (Hyp) residue. In connective tissue (such as bone, tendon, cartilage, ligament, skin, blood vessels, and teeth), individual collagen molecules are wound together in tight triple helices. These helices are organized into fibrils of great tensile strength, Jones & Miller, *J. Mol. Biol.*, 218:209–219 (1991). Varying the arrangements and cross linking of the collagen fibrils enables vertebrates to support stress in one-dimension (tendons), two-dimensions (skin), or three-dimensions (cartilage).

In vertebrates, the collagen polypeptide is translated with the typical repeat motif being ProProGly. Subsequently, in vivo, the hydroxylation of Pro residues is performed enzymatically after collagen biosynthesis but before the chains begin to form a triple helix. Thus, hydroxylation could be important for both collagen folding and collagen stability. The hydroxyl group of Hyp residues has long been known to increase the thermal stability of triple-helical collagen, Berg and Prockop, *Biochem. Biophys. Res. Comm.*, 52:115–120 (1973). For example, the melting temperature of a triple helix of (ProHypGly)$_{10}$ chains is 58° C., while that of a triple helix of (ProProGly)$_{10}$ chains is only 24° C., Sakakibara et al., *Biochem. Biophys. Acta,* 303:198–202 (1973). In addition, the rate at which (ProHypGly)$_{10}$ chains fold into a triple helix is substantially greater than the corresponding rate for (ProProGly)$_{10}$ chains, Chopra and Ananthanarayanan, *Proc. Natl. Acad. Sci. USA*, 79:7180–7184 (1982).

In general, molecular modeling based on the structure of triple-helical collagen and conformational energy calculations suggest that hydrogen bonds cannot form between the hydroxyl group of Hyp residues and any main chain groups of any of the collagen molecules in the same triple helix, Okuyama et al., *J. Mol. Biol.,* 152:247–443 (1981). Also, several models include the hypothesis that hydroxyproline increases the stability of collagen as a result a bridge of water molecules formed between the hydroxyl group and a main chain carbonyl group. For reviews of observations advancing this hypothesis, see: Suzuki et al., *Int. J. Biol. Macromol.,* 2:54–56 (1980), and Némethy, in *Collagen,* published by CRC press (1988), and the references cited therein.

However, there exists experimental evidence that is inconsistent with the bridging the water molecule model. For example, the triple helices of (ProProGly)$_{10}$ and (ProHypGly)$_{10}$ were found to be stable in 1,2-propanediol, and Hyp residues conferred added stability in these anhydrous conditions, Engel et al., *Biopolymers,* 16:601–622 (1977), suggesting that water molecules do not play a part in the added stability of (ProHypGly)$_{10}$. In addition, heat capacity measurements are inconsistent with collagen having more than one bound water per six Gly-X-Y units, Hoeve and Kakivaya, *J. Phys. Chem.,* 80:754–749 (1976). There exists no prior definitive demonstration of the mechanism by which the hydroxyproline residues stabilize collagen triplexes. Therefore, the molecular basis for these observed effects is still not clear, however, recent structural studies have begun to shed light on the structure and stability of collagen's triple-helix, see: Jenkins, C. L., Raines, R. T. *Nat. Prod. Rep.* 19: 49–59 (2002); and Raines, R. T., et al., *JACS,* 124:11, 2497–2505 (2002).

A better understanding of how the structure of collagen contributes to its stability would facilitate the design of a collagen or collagen mimics having improved stability. A highly stable collagen substitute could advance the development of improved wound healing treatments.

In recent years, there have been exciting developments in wound healing, including the development of tissue engineering and tissue welding. For example, autologous epidermal transplantation for the treatment of burns was a significant advance in tissue engineering. Tissue engineering has also led to the development of several types of artificial skin, some of which employ human collagen as a substrate. However, a major problem associated with this treatment is the fragile nature of these grafts during and after surgery.

Tissue welding is a wound healing technique in which a laser is used to thermally denature the collagen in the skin at the periphery of a wound. The wound is reannealed by permitting the renaturation of the collagen. In the case of large wounds, a "filler" or solder is required to effect reannealing of the wound. Various materials, including human albumin, have been used as solders for this purpose. A good solder is resilient and is non-immunogenic and should preferably be capable of interaction with native collagen in adjacent sites.

Collagen is also used for a variety of other medical purposes. For example, collagen is used in sutures which can be naturally degraded by the human body and thus do not have to be removed following recovery. A sometimes limiting factor in the design of collagen sutures is the strength of the collagen fibers. A collagen variant or mimic having a greater strength would aid in the usage of such collagen sutures by relieving this limitation.

What is needed in the art is a novel collagen having increased stability for use in artificial skin, as a solder in tissue welding, and as a general tool for use in the design of medical constituents.

It was previously shown that replacing Pro or Hyp in the Y position with 4 (R)Fluoroproline (Flp), first synthesized by Gottleib et al., *Biochemistry*, 4:11:2507–2513 (1965), greatly increases triple helix stability, see: U.S. Pat. No. 5,973,112; Holmgren, S. K., et al., *Nature* 392: 666–667 (1998); and Holmgren, S. K., et al., 6: 63–70 (1999). In contrast, it has been shown that replacing Pro or Hyp in the Yaa position with the diastereomer 4(S)-fluoroproline (flp) greatly decreases stability, see: Bretscher, L. E., et al., *J. Am. Chem. Soc.* 123:777–778 (2001).

SUMMARY OF THE INVENTION

The present invention is summarized in that a novel variant of collagen has been designed which forms a stronger triple helix than does native collagen. The novel variant which endows structural stability to collagen includes 4(S)-fluoroproline (flp) in the Xaa position of the triple helical collagen tripeptide having the formula $(Xaa\ Yaa\ Gly)_n$.

It is an object of the present invention to provide a novel, high stability collagen molecule that could be used as a component in artificial skin, as a solder in tissue welding, or as a substitute for collagen in other applications requiring high strength.

It is a feature of the present invention that evidence is provided to demonstrate the nature of the additional stability added to collagen by the proline residue, thereby making it possible to design other residues for that position which would add to that stability.

The present invention features a novel collagen mimic having increased strength and describes alternative methods by which that molecule can be made.

Other objects, advantages, and features of the present invention will become apparent upon review of the specification, drawings, and claims.

DETAILED DESCRIPTION OF THE INVENTION

Figure 1:
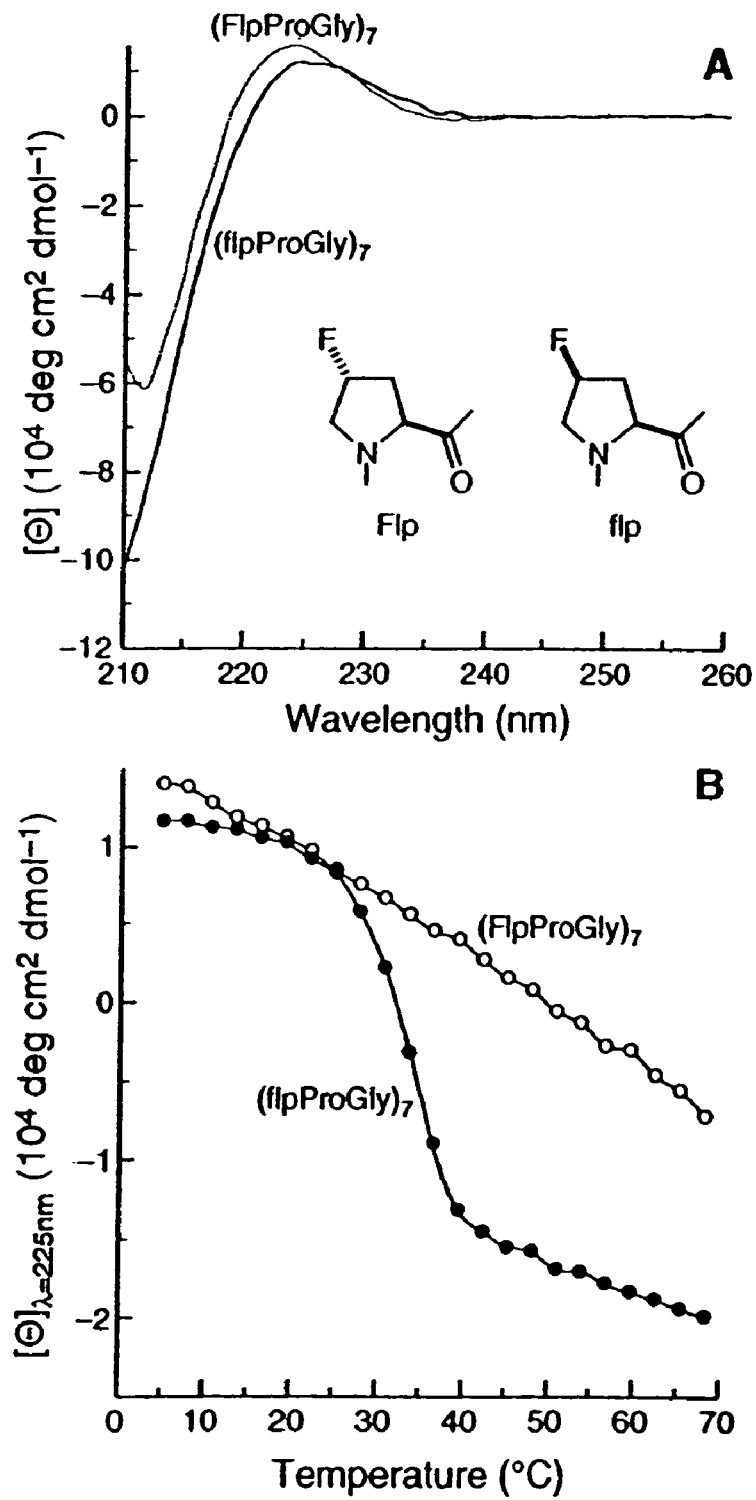
FIG. 1 shows the circular dichroism spectra of tripeptides $(flp-Pro-Gly)_7$ and $(Flp-Pro-Gly)_7$ at 5° C. (A) shows that $(flp-Pro-Gly)_7$ and not $(Flp-Pro-Gly)_7$ forms a stable triple helix. (B) shows that $(flp-Pro-Gly)_7$ has a cooperative transition characteristic of a triple helix unfolding upon thermal denaturation.

The investigation that lead to the work described here began with the notion that a better understanding of the factors that contribute to the three dimensional structure and stability of collagen would facilitate the design of a collagen variant having improved strength for use in wound healing, and the development of treatments for people suffering from collagen-related illnesses. It would also provide a general purpose stronger collagen for a variety of purposes.

The hypothesis underlying this study was the belief that bridging water molecules are unlikely to contribute significantly to collagen stability. First, immobilizing one or more water molecules for each Hyp residue would evoke an enormous entropic cost. A water molecule can form 4 hydrogen bonds. In bulk aqueous solution, these 4 hydrogen bonds are formed with other water molecules that are themselves mobile. In contrast, the bridging water molecules of collagen would suffer a far greater loss of entropy because two of their hydrogen bonds would be with collagen, which is immobile relative to a water molecule.

Second, if the bridging water molecules of collagen are indeed important for collagen stability, then it is likely that they would be homogeneous, with one hydrogen-bonding pattern predominating. However, a high-resolution three-dimensional structure of triple-helical collagen suggested that individual Hyp residues bond to 1, 2, 3, or 4 water molecules, forming irregular, complex networks of intrachain or interchain hydrogen bonds, Bella et al., *Science*, 266:75–81 (1994). This heterogeneity and complexity in the hydrogen bonding is inconsistent with the hypothesis that bridging water molecules confer stability to collagen.

Third, it is understood that the pucker of a pyrrolidine ring can be influenced by electronegative substitutents. This effect is stereoelectronic, as it depends on the configuration and electron-withdrawing ability of the substituent. In particular, the gauche effect exerted by an electron-withdrawing 4(R)-substituent stabilizes the Cγ-exo pucker, and that by a 4(S)-substituent stabilizes the Cγ-endo pucker. The degree of stabilization is greatest for fluorine, the most electronegative of atoms.

Furthermore, molecular modeling of a triple helix of $(ProProGly)_{10}$ strands has suggested that Pro in the Xaa and Yaa position prefers to adopt a Cγ-endo and Cγ-exo pucker, respectively. This pattern has been observed in the structure of a crystalline $(ProProGly)_{10}$ triple helix. The pyrrolidine ring pucker influences the range and distribution of the φ and ψ main-chain dihedral angles of Pro, and can fix those dihedral angles for optimal packing of the triple helix. Increasing the preference for the desired Cγ-exo conformation in the Yaa position by inclusion of either Hyp or Flp decreases the entropic penalty for triple-helix formation. Likewise, Hyp and Flp increase the preference of the ω main-chain dihedral angle for the trans (ω=180°) conformation. Because all of the peptide bonds in collagen are trans, preorganization of ω by Hyp and Flp decreases the entropic penalty for triple-helix formation.

As in the Yaa position, preorganization of ω in the trans conformation would also be favorable in the Xaa position. Yet, a Cγ-exo conformation favors φ and ψ dihedrals that are not ideal for this position. Hence, fixing the ring pucker of proline in the Xaa position could have a favorable influence on either φ, ψ or ω, but not all three.

The results obtained through these molecular modeling studies have been advanced by independent laboratory results obtained where Pro or Hyp in the Yaa position was replaced with 4(R)- fluoroproline (Flp), leading to greatly increased triple helix stability, see U.S. Pat No. 5,973,112. It is understood that this gain in stability results from the greater preference of Hyp and Flp to adopt Cγ-exo ring puckers due to stereoelectronic effects. In contrast, replacing Pro or Hyp in the Yaa position with the diastereomer 4(S)- fluoroproline (flp) greatly decreases collagen stability, see: Bretscher, L. E.; et al., *J. Am. Chem. Soc.*, 123, 777–778 (2001).

Proposed here is an alternative explanation for collagen stability that is based on the influence of inductive effects and stereoelectronic effects on collagen conformation and stability. To test this hypothesis, the effect of 4(S)-fluoroproline in the Xaa position of the collagen triple helix was analyzed and the thermal stabilities of (FlpProGly)$_7$ and (flpProGly)$_7$ were examined by circular dichroism spectroscopy. It was found as detailed in the examples that the same stereoelectronic effects cause the stereoisomer 4(S)-fluoroproline (flp) to prefer the Cγ-endo ring pucker.

Accordingly, this invention is based on the premise that both the electron withdrawing ability of a substituent and the stereoelectronic preference of Xaa are capable of increasing the stability of the collagen triple helix. The data presented here supports the hypothesis. The placement of the fluorine atom in the 4 position in the proline in 4(S)-fluoroproline (flp), and the incorporation of flp into the first position of the collagen triple helixes, as described below, does in fact increase the strength of the collagen triple helix formation. Thus the intelligent design of improved collagen mimics is enabled for the first time.

To test the role of the inductive effect on collagen stability, the collagen mimic (flp-Pro-Gly)$_7$ was synthesized, where flp is 4(S)-fluoro-L-proline, as described in detail in the examples below. In flp residues, the fluorine atom imposes a strong inductive effect, but does not form hydrogen bonds. The thermal stabilities and helicity of several collagen tripeptides were determined using circular dichroism. The collagen mimic (flpProGly)$_7$ was found to form a very stable triple helical collagen, stronger than either of the other forms tested, see Table 1. This demonstrates not only that the collagen mimic (flpProGly)$_7$ is useful as a collagen mimic for making collagen compatible materials, but that the critical parameter in the formation of the collagen triple helix structure is the inductive effect on electron density at the 4 position in the proline in the middle position of the triple repeat motif. Forms of collagen mimics having other amino acids at the second position in the triple motif is contemplated here.

The present invention is a collagen mimic comprising a triple repeat motif peptide having the formula (flpYaaGly)$_n$, where flp is 4(S)-fluoro-L-proline, n is a positive integer, and Yaa is any amino acid, but is typically one of the 20 naturally occurring amino acids. Yaa can also be a modified amino acid residue, meaning a naturally occurring amino acid residue modified by the addition of a small moiety such as a hydroxyl, fluorine, or other functional group. In the examples below, the collagen mimics that were synthesized and tested had a proline residue at position Yaa. It is anticipated that amino acids other than proline would be tolerated in the Yaa position, given that natural collagen has a wide variety of amino acids in the Yaa position, although proline would be the prototypical residue at that position. The residues in the Yaa position can be the same or can vary in identity along a single molecule.

The examples below describe among others the chemical synthesis of a collagen having the sequence (flpYaaGly)$_n$. The number of repeats of this motif can be three or seven or, alternatively, the entire collagen can be constructed from this tripeptide. The present invention is intended to encompass a molecule comprising the sequence, regardless of the mode of synthesis. It is anticipated that one skilled in the art of synthesizing biopolymers could make the peptide by using a modification of the chemical synthesis described below.

The molecule can be made by direct synthesis, as described below. It is also contemplated that the molecule can be made by fluorination of the prolines in native collagen, either by enzymatic modifications of the immature collagen form (ProProGly)$_n$ or by substitution of the hydroxyl group in Hyp in mature collagen (ProHypGly)$_n$, with a fluorine atom, as the diastereomer 4(S)-fluoroproline (flp) in the Xaa position.

It may become possible to obtain the collagen mimic having the flpYaaGly tripeptide repeat through biosynthesis, and this method of making this collagen mimic is contemplated here. Collagen mimics obtained by chemical and stereoelectronic modification of natural collagens are within the spirit and scope of the present invention.

The success of the present invention relies on the superior electron-withdrawing ability of fluorine, relative to the hydroxyl group of hydroxyproline and its sterioelectronic preference located at the Xaa position of collagen. It is therefore expected that a chemical modification that enhances the electron-withdrawing ability of the hydroxyl group (as opposed to replacing the hydroxyl group with a fluorine atom) as well as the stereoelectronic effects in the Xaa position in collagen will greatly enhance collagen stability. It is anticipated that chemical and a stereoelectronic modification to the hydroxyl group of hydroxyproline that increase its electron-withdrawing ability would result in a collagen mimic with increased stability. Proposed chemical and stereoelectronic modifications of the hydroxyl group of hydroxyproline are described below.

EXAMPLES

Synthesis of Defined Mimics of Triple-helical Collagen

In order to conduct the experiments the commercial chemicals that were utilized were of reagent grade or better, and were used without further purification. N-(tert-Butoxycarbonyl)-(2S,4S)-4-hydroxyproline benzyl ester (BocHypOBn, 1) was synthesized as described previously, see: Williams, M. A.; et al., *J. Org. Chem.* 59:3616–3625 (1994). Anhydrous THF, DMF, and CH$_2$Cl$_2$ were obtained from a CYCLE-TAINER® solvent delivery system (Baker). Other anhydrous solvents were obtained in septum-sealed bottles. Flash chromatography was performed with silica gel 60, 230–400 mesh (Silicycle). Preparative HPLC was performed with a Varian Dynamax C-18 reversed-phase column. Analytical HPLC was performed with a Vydac C-18 reversed-phase column. Linear gradients of solvent A (H$_2$O with 0.1% v/v TFA) and solvent B (CH$_3$CN with 0.1% v/v TFA) were used. Both $^1$H NMR (300 MHz) and $^{13}$C NMR (75.4 MHz) were obtained with a Bruker AC+ 300 spectrometer at the University of Wisconsin—Madison Chemistry Instrument Center. All NMR samples were in CDCl$_3$ unless indicated otherwise.

Synthesis of Collagen Mimic

Figure 2:
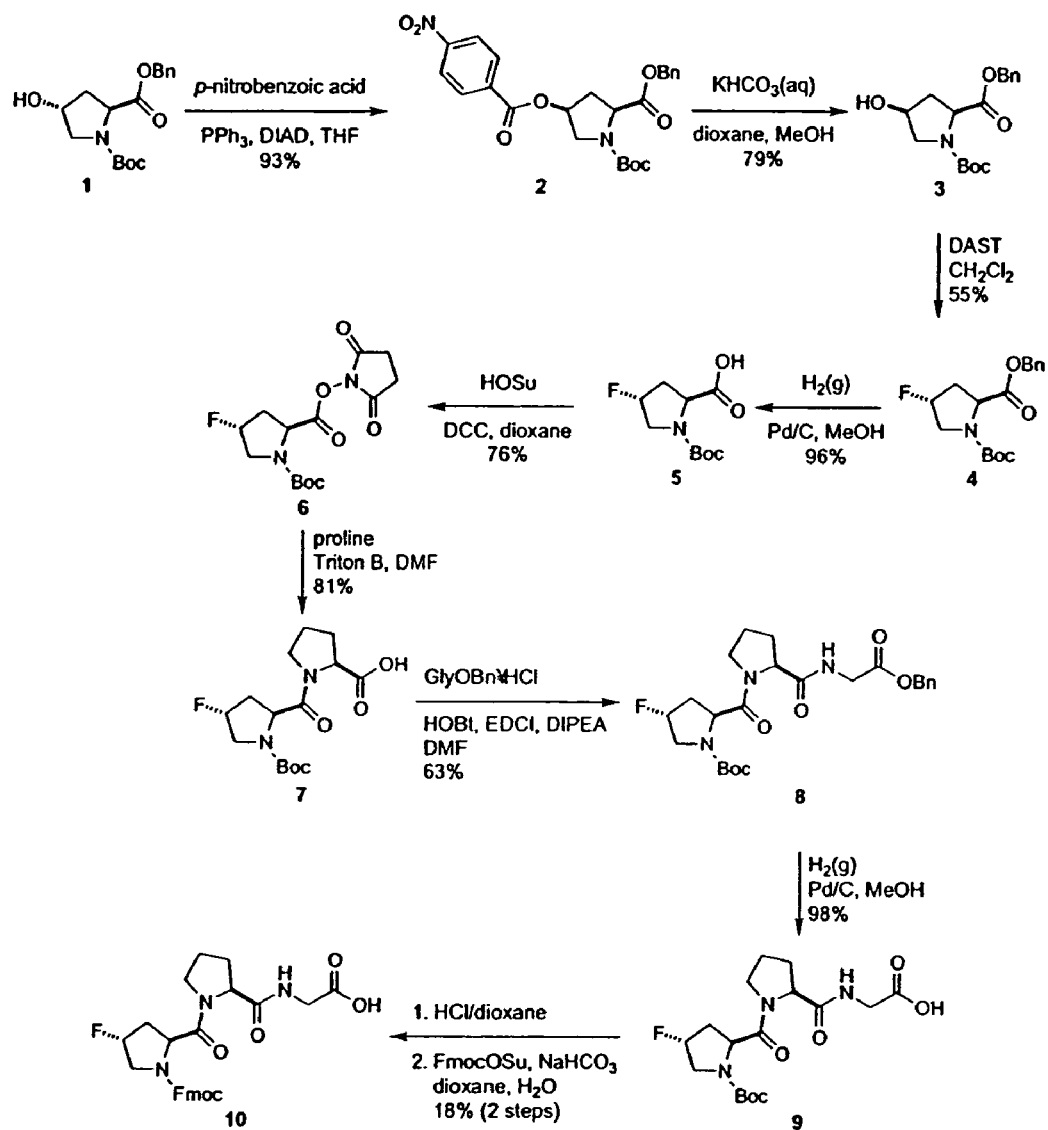
FIG. 2 illustrates the synthetic route for the production of N-[N-[N-(fluorenylmethoxycarbonyl)-(2S,4R)-4-fluoroprolyl]-2S-prolyl]-glycine.

In brief the synthetic route used to synthesize N-[N-[N-(fluorenylmethoxycarbonyl)-(2S,4R)-4-fluoroprolyl]-2S-prolyl]-glycine or otherwise referred to herein as Fmoc-flp-Pro-Gly, as described in Vitagliano, L., et al., *Biopolymers* 58: 459–464 (2001) is shown in FIG. 2.

In more detail, synthesis of the collagen mimic was performed using the following experimental procedures.

N-(tert-Butoxycarbonyl)-(2R,4S)-4-p-nitrophenoxyproline benzyl ester (2). BocHypOBn (1; 4.95 g, 15.4 mmol) was dissolved in dry THF under Ar(g). After cooling the solution in a 0° C. bath, PPh$_3$ (4.84 g, 18.5 mmol) and p-nitrobenzoic acid (3.07 g, 18.4 mmol) were added. This addition was followed by the slow (ca. 15-min) dropwise addition of a solution of DIAD (3.7 g, 18 mmol) in dry THF (10 mL). The resulting solution was stirred for 3 h and then concentrated to a yellow oil by rotary evaporation under reduced pressure. Adding chloroform to the oil resulted in the formation of colorless crystals that were isolated by vacuum filtration. TLC indicated that the crystals were not the desired product 2, but most likely triphenylphosphine oxide. The remaining material was purified by flash chromatography (1.5% v/v $CH_3OH$ in $CHCl_3$). Chromatography was repeated twice more to complete the separation of 2 from triphenylphosphine oxide and diisopropylhydrazine, and thus afford 2 (6.71 g, 14.3 mmol, 93%) as a colorless oil.

N-(tert-Butoxycarbonyl)-(2R,4S)-4-hydroxyproline benzyl ester (3). To a solution of 2 (6.5 g, 14 mmol) in dioxane (45 mL) was added a solution (110 mL) of $KHCO_3$ (0.5% w/v in 10% v/v aqueous methanol). After stirring for 14 h, the mixture was concentrated by rotary evaporation under reduced pressure, and the resulting oily solid was partitioned between $CHCl_3$ (100 mL) and water (50 mL). The aqueous layer was extracted further with $CHCl_3$ (2×20 mL), and the combined organic extracts were then washed with water (50 mL), dried over $MgSO_4$(s), and concentrated by rotary evaporation under reduced pressure. Flash chromatography (3% v/v $CH_3OH$ in $CHCl_3$) provided 4.33 g of a yellow oil. Analysis by $^1H$ NMR revealed that the oil consisted of a 3.6:1 mixture of 3 and N-(tert-butoxycarbonyl)-(2S,4S)-4-hydroxyproline methyl ester. Anticipating easier separation following fluorination, the mixture containing 3.6 g of 3 (11 mmol, 79%) and 0.75 g (3.0 mmol) of the methyl ester was used in the next step.

N-(tert-Butoxycarbonyl)-(2S,4R)-4-fluoroproline benzyl ester (4). A mixture of 3 (3.6 g, 11 mmol) and N-(tert-butoxycarbonyl)-(2S,4S)-4-hydroxyproline methyl ester (0.75 g, 3.0 mmol) was dissolved in 30 mL dry $CH_2Cl_2$ under Ar(g). The solution was cooled to −78° C., and diethylaminosulfur trifluoride (DAST; 5.6 mL, 42 mmol) was than added by syringe. The mixture was stirred for an additional 45 min at −78° C. and then allowed to warm to room temperature. After 20 h, the mixture was transferred to a separatory funnel and carefully washed with 80 mL of saturated $NaHCO_3$(aq). A considerable amount of gas was released during wash. The organic layer was washed with an additional 2×30 mL of saturated $NaHCO_3$(aq) and 30 mL of water, dried over $MgSO_4$(s), and concentrated to a dark oil by rotary evaporation at reduced pressure. Flash chromatography (hexanes/EtOAc 4:1) afforded 4 (1.98 g, 6.12 mmol, 55%) as an oily yellow solid.

N-(tert-Butoxycarbonyl)-(2S,4R)-4-fluoroproline (5). To a solution of 4 (1.98 g, 6.12 mmol) in $CH_3OH$ under Ar(g) was added 1.2 g of palladium on carbon (10% w/w, 1.1 mmol Pd). A balloon filled with $H_2$(g) was affixed to the reaction flask, and the black suspension was stirred under $H_2$(g) for 19 h. The mixture was filtered through a pad of Celite, and the colorless filtrate was concentrated to a colorless foam by rotary evaporation at reduced pressure. Compound 5 (1.37 g, 5.86 mmol, 96%) was used without further purification.

N-(tert-Butoxycarbonyl)-(2S,4R)-4-fluoroproline succinimide ester (6). N-Hydroxysuccinimide (0.74 g, 6.5 mmol) was added to a solution of 5 (1.37 g, 5.86 mmol) in dry dioxane (16 mL) under Ar(g). The mixture was cooled in a 0° C. bath causing it to become much more viscous. A solution of DCC (1.21 g, 5.87 mmol) in dry dioxane (34 mL) was added. During addition, the mixture became too viscous to stir magnetically, so it was removed from the 0° C. bath and allowed to warm as the remainder of the DCC solution was added. The reaction mixture was allowed to stir overnight at room temperature, and then placed in a freezer (−20° C.) for 24 h to facilitate complete precipitation of DCU. After thawing the mixture, the viscous white suspension was filtered under reduced pressure to remove DCU. The filtrate was concentrated to a beige solid by rotary evaporation under reduced pressure. This solid was recrystallized in isopropanol to afford 6 (1.47 g, 4.44 mmol, 76%) as colorless needles.

N-[N-(tert-Butoxycarbonyl)-(2S,4R)-4-fluoroprolyl]-2S-proline (7). Proline (0.55 g, 4.8 mmol) was added to 2.2 mL of a methanolic solution of benzyltrimethylammonium hydroxide (2.2 M), and the mixture was concentrated by rotary evaporation under reduced pressure. The flask containing the residual oil was flushed with Ar(g) before the addition of anhydrous DMF (50 mL) and 6 (1.45 g, 4.39 mmol). This solution was stirred under Ar(g) for 14 h, and then concentrated to an oil with an orange tint by rotary evaporation under reduced pressure. The oil was taken up in 5% w/v $KHCO_3$(aq) and washed with ethyl acetate. The aqueous layer was acidified to pH ~2 by addition of 2N HCl. The product was extracted with ethyl acetate, and the organic layer was dried over $MgSO_4$(s) and concentrated to a colorless foam by rotary evaporation under reduced pressure, affording 7 (1.18 g, 3.57 mmol, 81%).

N-[N-[N-(tert-Butoxycarbonyl)-(2S,4R)-4-fluoroprolyl]-2S-prolyl]-glycine benzyl ester (8). Glycine benzyl ester hydrochloride (0.76 g, 3.8 mmol) and HOBt (0.52 g, 3.8 mmol) were added to a solution of 7 (1.15 g, 3.48 mmol) in dry DMF (70 mL) under Ar(g). The colorless solution was cooled in a 0° C. bath before adding DIPEA (0.67 mL, 3.8 mmol), which caused the solution to turn cloudy, and EDCI (0.74 g, 3.8 mmol). The mixture was allowed to stir at room temperature overnight and then concentrated by rotary evaporation under reduced pressure. The resulting oil was dissolved in ethyl acetate (100 mL) and washed with 50 mL each of 5% w/v $KHCO_3$(aq), 5% w/v $KHSO_4$(aq), and water. The organic layer was dried over $MgSO_4$(s) and concentrated to a colorless oil by rotary evaporation under reduced pressure. Flash chromatography (35% v/v $CH_3CN$ in $CHCl_3$) afforded 8 (1.05 g, 2.20 mmol, 63%) as a colorless solid.

N-[N-[N-(tert-Butoxycarbonyl)-(2S,4R)-4-fluoroprolyl]-2S-prolyl]-glycine (9). Palladium on carbon (10% w/w, 0.41 g Pd/C, 0.39 mmol Pd) was added carefully to a solution of 8 (1.05 g, 2.19 mmol) in methanol (37 mL) under Ar(g). A balloon filled with $H_2$(g) was affixed to the reaction vessel, and the mixture was allowed to stir overnight under $H_2$(g). The mixture was filtered through a pad of Celite, and the filtrate was concentrated to a colorless solid by rotary evaporation under reduced pressure. The product 9 (0.83 g, 2.1 mmol, 98%) was used without further purification.

N-[N-[N-(Fluorenylmethoxycarbonyl)-(2S,4R)-4-fluoroprolyl]-2S-prolyl]-glycine (10). 4N HCl/dioxane (5 mL) was added under Ar(g) to 9 (0.83 g, 2.1 mmol), which dissolved quickly. After stirring for a few minutes, a sticky solid precipitated. After stirring for 1 h, a stream of air was used to evaporate the solvent and HCl. The sticky residue was dissolved in 18 mL of 10% w/v $NaHCO_3$(aq), forming a colorless solution that was cooled in a 0° C. bath. A solution of FmocOSu (0.70 g, 2.1 mmol) in dioxane (10 mL) was then added. The reaction mixture was stirred for 22 h and then concentrated by rotary evaporation under reduced pressure. The residue was partitioned between 50 mL of 5% w/v $KHCO_3$(aq) and 40 mL of $CHCl_3$, which produced a viscous opaque suspension. The entire mixture was acidified with 2N HCl until the pH of the aqueous layer was lowered to 1.5 which resulted in dissolution of the suspension. The layers were separated, and the aqueous layer was extracted further with $CHCl_3$ (2×30 mL). The combined organic extracts were washed with brine (25 mL), dried over $MgSO_4(s)$, and concentrated to a colorless foam at reduced pressure. Attempts to purify this foam (1.09 g) by recrystallization were unsuccessful. Preparatory HPLC (linear gradient: 20–50% v/v B over 30 min) was used to isolate 10 (0.19 g, 0.37 mmol, 18%) as a colorless solid.

Synthesis of Flp-flp-Gly

Figure 3:
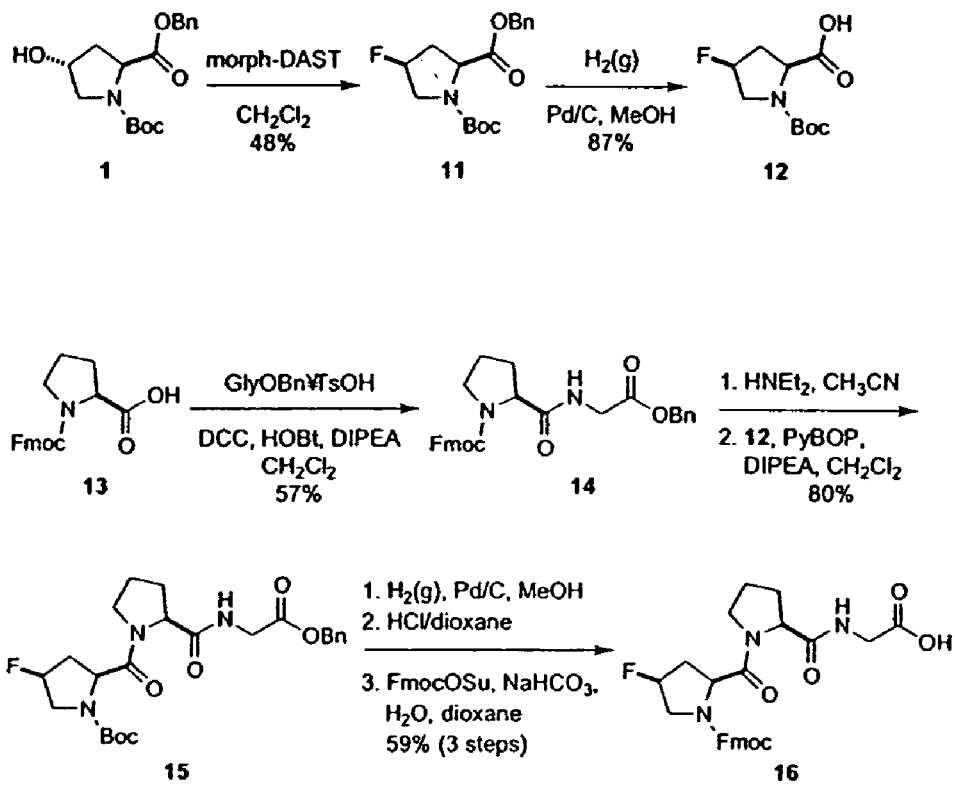
FIG. 3 illustrates the synthetic route for the production of N-[N-(N-tert-fluorenylmethoxycarbonyl-(2R,4S)-4-fluoroprolyl)-2S-prolyl]-glycine as described in Kramer, R. Z., et al., *Nat. Struct. Biol.* 6: 454–457 (1999) and in the examples below.

In brief the synthetic route used to synthesize N-[N-(N-tert-fluorenylmethoxycarbonyl-(2R,4S)-4-fluoroprolyl)-2S-prolyl]-glycine or otherwise referred to herein as Fmoc-flp-Pro-Gly, as described in Kramer, R. Z., et al., *Nat. Struct. Biol.* 6: 454–457 (1999) shown in FIG. 3.

In more detail, synthesis of the collagen mimic was performed using the following experimental procedures.

N-tert-Butoxycarbonyl-(2R,4S)-4-fluoroproline benzyl ester (11). Morpholinosulfur trifluoride (morph-DAST; 3.5 mL, 29 mmol) was added by syringe to a solution of 1 (6.5 g, 20 mmol) in dry $CH_2Cl_2$ (200 mL) under Ar(g) at −78° C. The solution w allowed to warm to room temperature and stirred overnight. Following a quench with methanol, the reaction mixture was washed with 2×100 mL saturated $NaHCO_3$(aq). An emulsion resulted, so the mixture was diluted with $H_2O$ and $CH_2Cl_2$ and filtered through Celite. The biphasic filtrate was separated, and the organic layer was washed with water, dried over $MgSO_4$(s), and concentrated by rotary evaporation under reduced pressure. The resulting oil was purified by flash chromatography (1.5% v/v MeOH in $CH_2Cl_2$), which afforded 11 (3.1 g, 9.6 mmol, 48%) as a yellow oil. An additional 2.32 g of 11 that were contaminated with a minor impurity, as indicated by TLC, were also obtained from the column.

N-tert-Butoxycarbonyl-(2S,4S)-4-fluoroproline (12). Methanol (95 mL) was carefully added to a mixture of 11 (2.8 g, 8.7 mmol) and palladium on carbon (10% w/w, 1.0 g, 0.94 mmol Pd) under Ar(g). A balloon filled with $H_2$(g) was affixed to the reaction flask, and the mixture was stirred overnight. After 24 h, unreacted starting material remained, so an additional 0.95 g (0.89 mmol Pd) of Pd/C were added and a fresh balloon filled with $H_2$(g) was placed on the flask. After stirring overnight, TLC indicated reaction had gone to completion, and the mixture was filtered through Celite. The filtrate was concentrated to a white solid by rotary evaporation under reduced pressure and dried under vacuum, affording 12 (1.8 g, 7.6 mmol, 87%), which was used without further purification.

N-(N-Fluorenylmethoxycarbonyl-2S-prolyl)-glycine benzyl ester (14). To a solution of N-fluorenylmethoxycarbonyl-2S-proline (13) (3.37 g, 9.99 mmol) in 100 mL of dry $CH_2Cl_2$ under Ar(g) were added HOBt•$H_2O$ (1.53 g, 9.99 mmol) and DCC (2.06 g, 9.99 mmol). Within minutes, the solution became viscous and opaque. After 20 min, glycine benzyl ester tosylate (3.65 g, 14.8 mmol) and DIPEA (1.7 mL, 9.8 mmol) were added to the mixture. The mixture was stirred for 6 h and then filtered under vacuum to remove DCU. More DCU precipitated from the filtrate, so it was filtered a second time. The filtrate was then washed with 100 mL each of 5% w/v $KHCO_3$(aq), 5% w/v $KHSO_4$(aq), and water. The organic layer was dried over $MgSO_4$(s), and concentrated by rotary evaporation under reduced pressure. The oily residue was purified by flash chromatography (hexanes/EtOAc 1:1.4) and then crystallized from EtOAc/hexanes, which afforded 2.74 g (5.65 mmol, 57%) of 14 as an off-white powder.

N-[N-(N-tert-Butoxycarbonyl-(2S,4S)-4-fluoroprolyl)-2S-prolyl]-glycine benzyl ester (15). Diethylamine (6 mL, 60 mmol) was added with stirring to a solution of 14 (0.73 g, 1.5 mmol) in $CH_3CN$ (50 mL). After 90 min, the solution was concentrated to an oil by rotary evaporation under reduced pressure. The reaction vessel was filled with Ar(g), and the oil was then dissolved in dry $CH_2Cl_2$ (25 mL). Compound 12 (0.35 g, 1.5 mmol), PyBOP (0.78 g, 1.5 mmol), and DIPEA (0.78 mL, 4.5 mmol) were then added. The resulting solution was stirred for 14 h and then concentrated by rotary evaporation under reduced pressure. The resulting oil was dissolved in EtOAc (100 mL) and washed with 5% w/v $KHSO_4$ (aq; 3×50 mL). The organic layer was then diluted with 30 mL $CH_2Cl_2$ to dissolve material that had oiled out and washed with water (50 mL). After drying over $MgSO_4$(s) and concentrating by rotary evaporation under reduced pressure, the resulting oil was purified by flash chromatography (3% v/v $CH_3OH$ in $CH_2Cl_2$) affording 15 (0.57 g, 1.2 mmol, 80%). Chromatography did not remove two minor impurities, as indicated by TLC, but crude 15 was used without further purification.

N-[N-(N-tert-Fluorenylmethoxycarbonyl-(2S,4S)4-fluoroprolyl)-2S-prolyl]-glycine (16). Crude 15 (0.57 g, 1.2 mmol) was mixed with palladium on carbon (10% w/w, 0.23 g, 0.22 mmol Pd) under Ar(g). Methanol (20 mL) was carefully added to the mixture. A balloon filled with $H_2$(g) was affixed to the reaction vessel, and the mixture was stirred overnight (17 h). The mixture was filtered through Celite, and the filtrate was concentrated to a solid by rotary evaporation under reduced pressure. The mass of crude BocflpProGly was 0.43 g (1.1 mmol). A solution of 4 N HCl in dioxane (5 mL) was added to the solid, causing it to dissolve. Within a few minutes, a sticky white solid began to form on the sides of the flask. After 2 h, the mixture was concentrated by rotary evaporation under reduced pressure, taken up in dioxane (~10 mL), and concentrated again by rotary evaporation under reduced pressure. The colorless residue was dissolved in water (6 mL), and then dioxane (12 mL) was added to the solution. To the stirred mixture was added FmocOSu (0.37 g, 1.1 mmol) followed by $NaHCO_3$ (0.28 g, 3.3 mmol). After stirring for 13 h, the mixture was concentrated by rotary evaporation under reduced pressure, and the resulting oil was dissolved in 5% w/v $KHSO_4$ (aq; 90 mL). The solution was washed with ethyl acetate (3×35 mL) and then acidified by addition of 2N HCl until a pH ~2 was obtained. The product was then extracted with $CH_2Cl_2$ (3×35 mL). The organic layer was washed with 5% w/v $KHSO_4$ (aq; 2×20 mL) and then concentrated to an oil by rotary evaporation under reduced pressure. Trituration with methanol resulted in a white solid that was recrystallized from methanol providing 16 as colorless needles (0.36 g, 0.71 mmol, 59%).

Collagen Mimic Tripeptide Purification Procedures

Attachment of FmocflpProGly (16) to 2-chlorotrityl resin. Under Ar(g), 160 mg (0.17 mmol) of 2-chlorotrityl resin (loading: 1.04 mmol/g) were swelled in dry $CH_2Cl_2$ (2 mL). A solution of 16 (52 mg, 0.10 mmol) and DIPEA (0.070 mL, 0.40 mmol) in dry $CH_2Cl_2$ (1.6 mL) was added by syringe. An additional 1 mL of dry $CH_2Cl_2$ was used to ensure complete transfer. After 90 min, 1 mL of anhydrous $CH_3OH$ was added to the mixture to cap any remaining active sites on the resin. The resin-bound peptide was isolated by gravity filtration, washed with several portions of dry $CH_2Cl_2$ (~10 mL), and dried at reduced pressure over KOH. The mass of the resin-bound peptide was 193 mg. Loading was measured by ultraviolet spectroscopy to be 0.46 mmol/g, see: Applied Biosystems. *Determination of the Amino Acid Substitution*

*Level via an Fmoc Assay;* Technical Note 123485 Rev 2; Documents on Demand—Applied Biosystems Web Page. http://docs.appliedbiosystems.com/search.taf (accesssed April 2003).

Attachment of FmocFlpProGly (10) to 2-chlorotrityl resin. Tripeptide 10 was loaded onto 2-chlorotrityl resin in similar fashion to that described for 16.

Synthesis of (FlpProGly)$_7$ and (flpProGly)$_7$.

The two 21-mer peptides were synthesized by segment condensation of the corresponding Fmoc-tripeptides (10 and 16) on solid phase using an Applied Biosystems Synergy 432A Peptide Synthesizer at the University of Wisconsin—Madison Biotechnology Center. The first trimer was loaded onto resin as described above. Fmoc-deprotection was accomplished by treatment with 20% (v/v) piperidine in DMF. The trimers were converted to active esters by treatment with HBTU, DIPEA, and HOBt. All couplings were allowed to occur for 45–60 min at room temperature.

Preparative HPLC was used to purify both peptides, (FlpProGly)$_7$ (gradient: 15% B to 45% B over 40 min) and (flpProGly)$_7$ (gradient: 10% B to 50% B over 45 min). Analysis by analytical HPLC (gradient: 10% B to 50% B over 60 min) and MALDI-TOF determined both peptides to be ≧90% pure.

Stability of Collagen Mimic Triple Helix

Circular Dichroism of (FlpProGly)$_7$ and (flpProGly)$_7$

To search for a stereoelectronic effect in the Xaa position on collagen stability, the tripeptides, (FlpProGly)$_7$ and (flpProGly)$_7$ were analyzed by circular dichroism. The peptides were dried under vacuum for at least 48 h before weighing and dissolving in 50 mM acetic acid. Concentrations were confirmed by measuring the absorbance of the solutions at 214 nm (□=6.4×10$^4$ M$^{-1}$ cm$^{-1}$). Bretscher, L. E.; et al., *J. Am. Chem. Soc.*, 123, 777–778 (2001). The solutions were allowed to incubate at ≦4° C. for at least 24 h before their CD spectra were acquired using an Aviv 62A DS Circular Dichroism Spectrometer at the University of Wisconsin—Madison Biophysics Instrumentation Facility (http://www-.biochem.wisc.edu/bif). Spectra were measured with a 1 nm bandpass. During the denaturation experiments, CD spectra were acquired at intervals of 3° C. At each temperature, the solutions were allowed to equilibrate for a minimum of 5 min before data was collected.

The Circular Dichroism (CD) spectra indicates that (flpProGly)$_7$ and not (FlpProGly)$_7$ forms a stable triple helix (FIG. 1A). The data obtained from the CD spectra indicates that only (flpProGly)$_7$ shows the cooperative transition characteristic of triple helix unfolding upon thermal denaturation (FIG. 1B). The midpoint of this transition is at 33° C. (Table 1).

Sedimentation Equilibrium of (FlpProGly)$_7$ and (flpProGly)$_7$.

Sedimentation equilibrium experiments were performed with a Beckman XL-A Analytical Ultracentrifuge at the University of Wisconsin—Madison Biophysics Instrumentation Facility (http://www.biochem.wisc.edu/bif). Samples were diluted to approximately 0.1 mM in 50 mM acetic acid, and then allowed to equilibrate at ≦4° C. for at least 24 h. Double-sector charcoal-filled Epon centerpieces with 3-mm path lengths were used. (The short path lengths reduce the total absorbance of the acetic acid buffer.) Equilibrium data were collected at multiple speeds at both 4 and 37° C. Gradients were monitored at 220 nm. A partial specific volume of 0.684 cm$^3$/g was calculated by composition with a correction for the fluorine atoms, see: Reynolds, J. A.; McCaslin, D. R. *Methods Enzymol.* 117, 41–53 (1985); and Durchschlag, H.; Zipper, P. *Prog. Colloid Polymer Sci.*, 94, 20–39 (1994).

Solvent densities of 1.000528 and 0.993546 g/mL at 4 and 37° C., respectively, were measured by an Anton Paar DMA5000 density meter. Data were analyzed with programs written for IgorPro (Wavemetrics) by Dr. Darrell R. McCaslin (University of Wisconsin—Madison Biophysics Instrumentation Facility).

Figure 4:
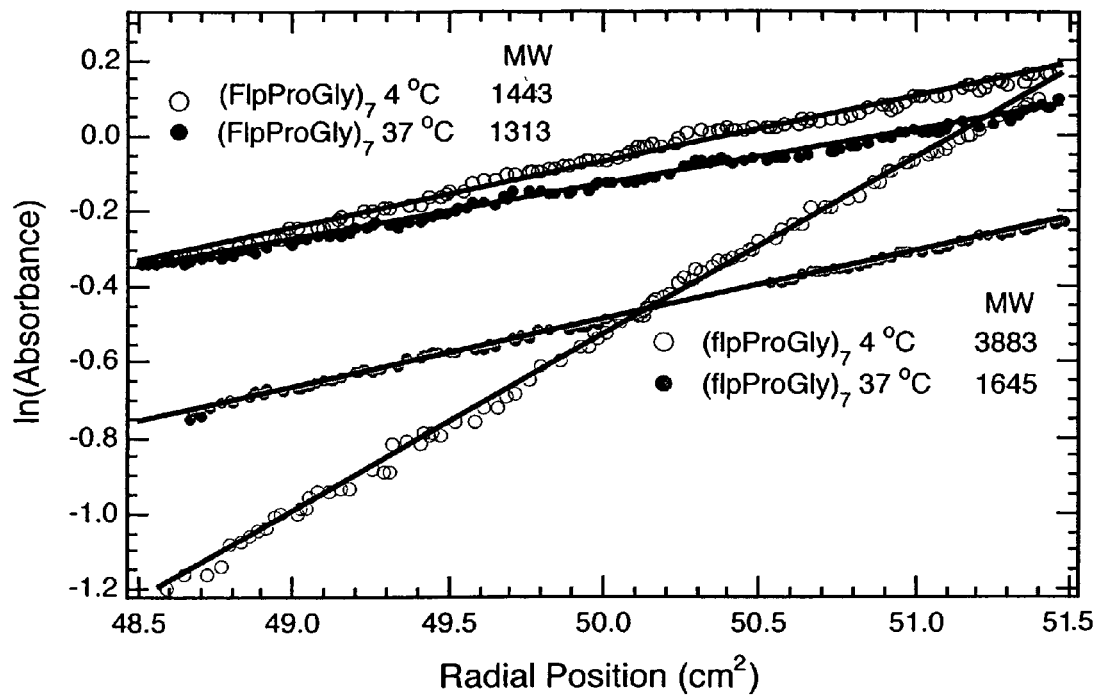
FIG. 4 illustrates the sedimentation equilibrium data for $(flpProGly)_7$ and $(FlpProGly)_7$ at a rotor speed of 40,000 rpm.

A semilog plot of the absorbance versus the square of the distance from the center of rotation is shown in FIG. 4. In this plot, the slope at any point is proportional to molecular weight. A single ideal species is characterized as a single molecular weight at all speeds and concentrations. At both temperatures, (FlpProGly)$_7$ appears to be a monomer. Equilibrium data were collected at 4° C.) and 37° C. Gradients were monitored at 220 nm. Apparent molecular weights determined from these data, assuming a partial specific volume of 0.684 cm$^3$/g, are shown.

The apparent molecular weights calculated from these plots are lower than expected (calculated MW 1903, vide infra) but are more consistent with a monomeric species than a complex. At 4° C., (flpProGly)$_7$ appears to exist as a complex. From these plots, its apparent molecular weight is 2.7-fold greater than that of (FlpProGly)$_7$. Thus, (flpProGly)$_7$ appears to be a trimer at 4° C., consistent with CD data (FIG. 1). The presence of a small amount of monomeric (flpProGly)$_7$ at 4° C. could make the observed mass appear to be 2.7- rather than 3.0-fold greater than that of (FlpProGly)$_7$. Raising the temperature to 37° C. causes a reduction in the molecular weight of (flpProGly)$_7$ to one similar to that of (FlpProGly)$_7$ at either 4 or 37° C. These data indicate that the (flpProGly)$_7$ trimer unfolds to monomers at ≦37° C., again consistent with CD data (FIG. 1).

All of the apparent molecular weights are somewhat lower than expected. This discrepancy can be attributed to several factors. First, the estimation of the partial specific volume (0.684 cm$^3$/g) could be incorrect, thus lowering the apparent molecular weights. Second, both peptides display non-ideal sedimentation behavior, which likely results from their shape being rod-like rather than spherical. Regardless, the sedimentation equilibrium data indicate that (flpProGly)$_7$ but not (FlpProGly)$_7$ forms a triple helix at 4° C., in gratifying agreement with the CD data.

A summary of these results is shown in Table 1, illustrating the effects of 4-Hydroxyproline and 4-Fluoroproline diastereomers on the conformational stability of a collagen triple helix with (XaaYaaGly)$_7$ strands.

TABLE 1

Effects of 4-Hydroxyproline and 4-Fluoroproline Diastereomers on the Conformational Stability of a Collagen Triple Helix with (XaaYaaGly)$_7$ Strands

| | $T_m$(° C.)[a] | |
|---|---|---|
| Xaa/Yaa | (XaaProGly)$_7$ | (ProYaaGly)$_7$ |
| Flp | no helix | 45[e] |
| Hyp | no helix[b] | 36[e] |
| Pro | 6–7[c] | 6–7[c] |
| hyp | no helix[d] | no helix[f] |
| flp | 33 | no helix[e] |

[a]Temperature at the midpoint of the thermal transition as measured by CD spectroscopy. "No helix" refers to $T_m$ < 5° C.
[b]Reported for (HypProGly)$_{10}$, Resnati, G. Tetrahedron 49:9385–9445 (2000).

TABLE 1-continued

Effects of 4-Hydroxyproline and 4-Fluoroproline Diastereomers on the Conformational Stability of a Collagen Triple Helix with (XaaYaaGly)$_7$ Strands

| Xaa/Yaa | $T_m$ (° C.)[a] | |
|---|---|---|
| | (XaaProGly)$_7$ | (ProYaaGly)$_7$ |

[d]Reported for (hypProGly)$_{10}$, Shaw, B. R. et al., J. M. Biopolymers 14:1951–1985 (1975).
[e]Reported for (hypProGly)$_{10}$, in Inouye, K., et al., J. Arch. Biochem. Biophys. 219:198–203 (1982).
[f]Reported for (ProhypGly)$_{10}$, in Inouye, K., et al., J. Biochem. Biophys. Acta 420:133–141 (1976).

Table 1 indicates that the degree of stabilization is greatest for fluorine, the most electronegative of atoms. Furthermore, Table 1 indicates that stereoelectronic effects can operate in the Xaa position of collagen. In the Xaa position flp is able to preorganize the φ and ψ dihedrals as in a triple helix without encountering the steric interactions that appear to plague hyp in this position. Moreover, the 4(S)- substituent in the Xaa position has limited access to solvent, thus making fluorine better suited than hydroxyl to occupy the Xaa position. Accordingly, the gain in stability upon replacing hyp with flp in the Xaa position exceeds that of replacing Hyp with Flp in the Yaa position (Table 1).

The results in Table 1 also suggest that the conformational stability of a (flpProGly)$_7$ triple helix is less than that of a (ProFlpGly)$_7$ triple helix. Two factors could contribute to this lower stability. First, Flp in the Yaa position causes favorable preorganization of all three main chain dihedral angles (φ,ψ,ω). In the Xaa position, flp increases the probability of ω adopting a cis (ω=0°) conformation, thus mitigating somewhat the benefit accrued from the preorganization of φ and ω. Second, a $C_δ$-endo pucker is already favored in Pro, and flp only increases that preference. In contrast, Flp has the more dramatic effect of reversing the preferred ring pucker, thereby alleviating the entropic penalty of triple-helix formation to a greater degree.

These results also suggest that there is a stereoelectronic preference for the 4(S)-fluoroproline (flp) diastereomer at the Xaa position for the collagen mimic tripeptide (XaaYaaGly)$_n$ in contrast to that of the Yaa position which endows more stability to the triple helix. It appears that in addition to the fact that electron-withdrawing ability of the fluorine atom increases the stability of the collagen triple helix, the results of the present invention advance the hypothesis that the pucker of a pyrrolidine ring can be influences by electronegative substituents. This effect is stereoelectronic as it depends on the configuration and electron-withdrawing ability of the substituent. In particular, it appears that the gauche effect exerted by an electron-withdrawing 4(R)-substituent stabilizes the $C_δ$-exo pucker, and that a 4(S)-substituent stabilizes the $C_δ$-endo pucker.

Because the stability of (flpProGly)$_7$ exceeds that of (FlpProGly)$_7$, the preorganization of φ and ψ in the Xaa position appears to be more important than is the preorganization of ω. This constraint could be less important for proline-poor regions of the triple helix, in which a non-proline residue occupies the Xaa or Yaa position. The structure of the crystalline collagen mimic indicates that proline-rich and proline-poor regions have a distinct triple-helical twist, which suggests that the factors that control stability could differ for these regions. Indeed it has been shown that replacement of proline in the Xaa position with Hyp does increase the stability of a proline-poor region, see: Bann, J. G. et al., *J. Biol. Chem.* 275: 24466–24469 (2000).

We claim:

1. A collagen mimic comprising a tripeptide having the formula:
   (flp-Yaa-Gly)n,
   where Yaa is any amino acid residue or any modified amino acid residue,
   flp is 4(S)-fluoroproline,
   and n is a positive integer.

2. The peptide of claim 1, wherein n is at least 3.

3. The peptide of claim 1, wherein n is at least 7.

4. A composition of matter comprising a triple helix of collagen mimic molecules in which each of the molecules in the helix comprises tripeptides of the formula:
   (flp-Yaa-Gly)n,
   where Yaa is any amino acid residue or a modified amino acid residue,
   flp is 4(S)-fluoroproline, and
   n is a positive integer.

5. A composition of matter as claimed in claim 4 wherein n is at least 3.

6. A composition of matter as claimed in claim 4 wherein Yaa is proline and n is at least 7.

7. The peptide of claim 4, wherein the Yaa residue is selected from the group consisting of 4(R)-hydroxyproline or an O-modified 4(R)-hydroxyproline.

8. A collagen mimic peptide comprising a tripeptide having the formula (flp-Pro-Gly)n.

9. The peptide of claim 8, wherein n is at least 3.

10. The peptide of claim 8, wherein n is at least 7.

* * * * *